US009360435B2

(12) United States Patent
Yates et al.

(10) Patent No.: US 9,360,435 B2
(45) Date of Patent: Jun. 7, 2016

(54) OPTICAL VIDEO MEASUREMENT SYSTEM HAVING INTERCHANGEABLE OPTICS

(71) Applicant: The L.S. Starrett Company, Athol, MA (US)

(72) Inventors: Robert Yates, Newport Beach, CA (US); Chengwu Deng, Irvine, CA (US); Mark Arenal, Mission Viejo, CA (US)

(73) Assignee: THE L.S. STARRETT COMPANY, Athol, MA (US)

( * ) Notice: Subject to any disclaimer, the term of this patent is extended or adjusted under 35 U.S.C. 154(b) by 420 days.

(21) Appl. No.: 13/889,293

(22) Filed: May 7, 2013

(65) Prior Publication Data

US 2014/0146162 A1    May 29, 2014

Related U.S. Application Data

(60) Provisional application No. 61/643,615, filed on May 7, 2012.

(51) Int. Cl.
| G01N 21/88 | (2006.01) |
| G01B 11/02 | (2006.01) |
| G01B 11/24 | (2006.01) |

(52) U.S. Cl.
CPC ............ *G01N 21/8806* (2013.01); *G01B 11/02* (2013.01); *G01B 11/2433* (2013.01)

(58) Field of Classification Search
CPC . G01N 21/8806; G01B 11/02; G01B 11/2433
USPC .......................................... 348/360, 373, 374
See application file for complete search history.

(56) References Cited

U.S. PATENT DOCUMENTS

| 4,247,190 A * | 1/1981 | Hashimoto ............ G03B 17/14 359/828 |
| 2004/0085453 A1* | 5/2004 | Gladnick ........... H04N 5/23209 348/207.99 |
| 2006/0055820 A1* | 3/2006 | Lyon ................ G08B 13/19619 348/373 |
| 2010/0225666 A1 | 9/2010 | Beauchemin |
| 2011/0001973 A1 | 1/2011 | Polidor et al. |

FOREIGN PATENT DOCUMENTS

GB          2392735        10/2005

* cited by examiner

*Primary Examiner* — Jefferey Harold
*Assistant Examiner* — Humam Satti
(74) *Attorney, Agent, or Firm* — Grossman, Tucker, Perreault & Pfleger, PLLC

(57) ABSTRACT

An optical video measurement system for comparing a manufactured part against a representation of the manufactured part. The measurement platform system includes an optical video system for capturing images of the manufactured part. The optical video system includes a camera configured to capture one or more images of the manufactured part. The camera is configured to cooperate with one of several interchangeable lens assemblies for providing optics for the camera. The camera is configured to receive and retain one of the several interchangeable lens assemblies by way of a bayonet mount, wherein each of the interchangeable lens assemblies includes a male side configured to be received within a female side of the camera. The video measurement system further includes a mounting assembly configured to receive and retain a portion of each of the interchangeable lens assemblies and maintain alignment of each of the interchangeable lens assemblies with the camera.

20 Claims, 7 Drawing Sheets

US 9,360,435 B2

OPTICAL VIDEO MEASUREMENT SYSTEM HAVING INTERCHANGEABLE OPTICS

CROSS-REFERENCE TO RELATED APPLICATIONS

The present non-provisional application claims the benefit of U.S. Provisional Patent Application Ser. No. 61/643,615, filed May 7, 2012, the entire disclosure of which is incorporated herein by reference.

FIELD

The present disclosure relates generally to measurement systems, and, more particularly, to a digital video measurement system having interchangeable telecentric video optics for imaging a manufactured part and measuring the manufactured part and/or comparing the manufactured part to an electronic design template and/or other representations of the manufactured part.

BACKGROUND

Optical metrology (i.e. the science of measurement) may be particularly important in the manufacturing industry. For example, certain manufactured parts may require specific dimensions (e.g. measurements). Although a design template used in the manufacturing of a part may include exact measurements, the actual dimensions of a manufactured part may deviate. As such, it is important that the actual dimensions of a manufactured part be measured or compared to a design template in order to ensure accuracy and consistency in the manufacturing process.

An optical video imaging platform (sometimes referred to as a comparator) is a device that applies the principles of optics to the inspection of manufactured parts. Generally, in a comparator, a magnified image of a manufactured part (such as a silhouette of the part) may be captured by a camera array and then projected upon a display screen and the dimensions and geometry of the part may be measured against prescribed limits. Generally, an optical comparator system includes one or more light sources, a support for the manufactured part, and optics, including a camera array, for capturing the image of the part and displaying the same onto a display screen, such as a monitor. The dimensions (e.g. measurements) of the manufactured part may be compared with the dimensions of a design template or to a calibrated linear or measurement standard to determine any inaccuracies and/or defects in the manufacturing of the part.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

DETAILED DESCRIPTION

The present disclosure is generally directed to a digital optical video measurement system for comparing a manufactured part against a digital representation of the manufactured part or to a calibrated measurement standard related to the part. The measurement system includes one or more light sources for imparting light upon the manufactured part, a support for the manufactured part, and an optical video system for capturing images of the manufactured part. The measurement system further includes a display for presenting the captured digital images of the manufactured part and a digital representation (e.g. CAD file) of the manufactured part.

The optical video system includes a digital camera configured to capture one or more images of the manufactured part. The camera is configured to cooperate with one of several interchangeable lens assemblies for providing optics for the camera. The camera is configured to receive and retain one of the several interchangeable lens assemblies by way of a bayonet mount. The video measurement system further includes a mounting assembly configured to receive and retain a portion of an interchangeable lens assembly and to maintain alignment of the interchangeable lens assembly with the digital camera. The digital camera and mounting assembly may be configured to receive a variety of interchangeable lenses, each having a universal coupling means.

A digital video measurement system consistent with the present disclosure may allow a variety of interchangeable lenses (e.g., but not limited to, lenses of different magnifications), each having a universal coupling means, to be relatively quickly and easily coupled to and decoupled from the mounting assembly and digital camera as desired. The universal coupling means of each of the interchangeable lens may provide a secure and consistent connection between the lens and the camera and mounting assembly, thereby maintaining accuracy of the digital camera without requiring recalibration when changing the lens.

Figure 1:
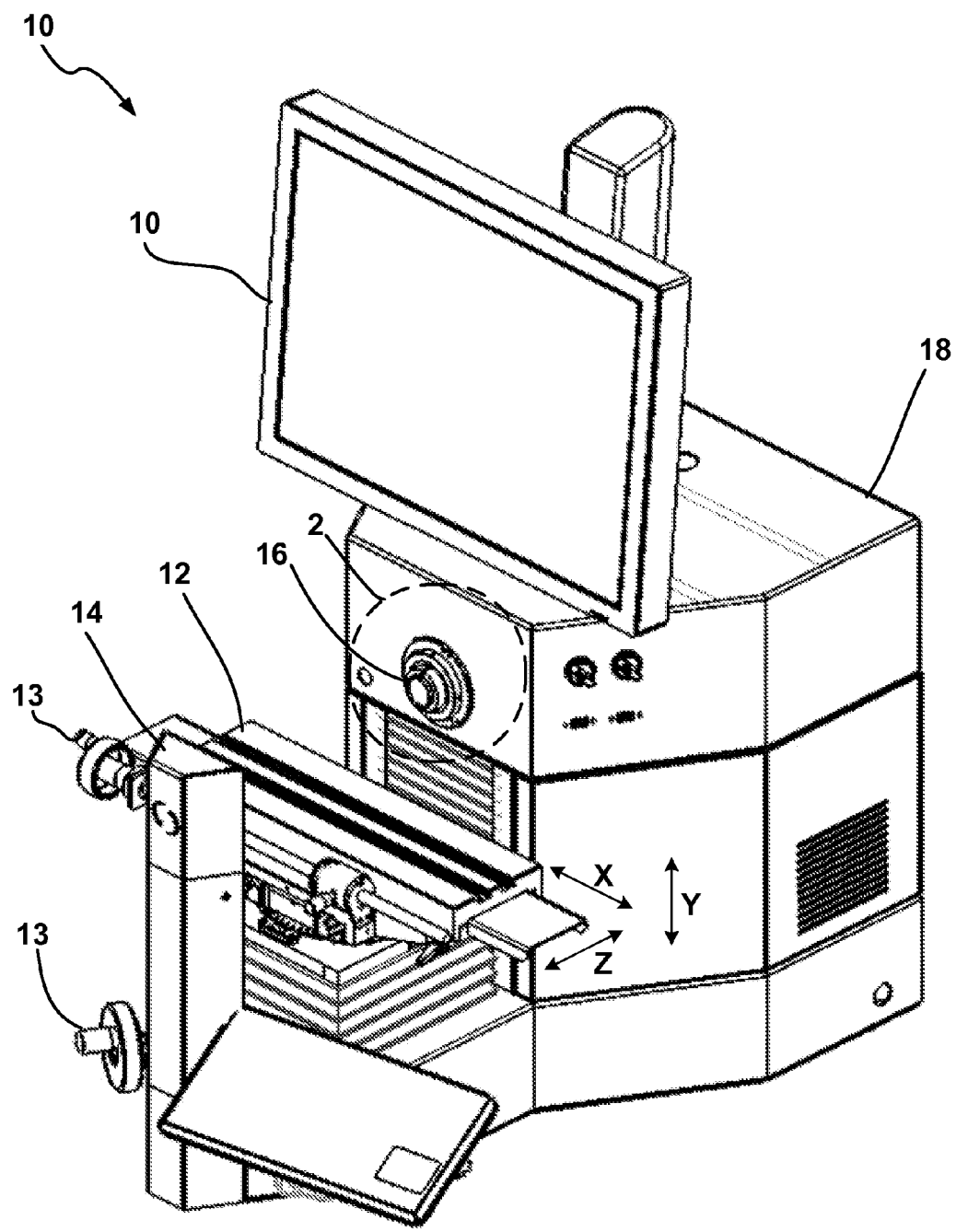
FIG. 1 is a perspective view of a digital video measurement system consistent with the present disclosure.

Turning to FIG. 1, a perspective view of a video measurement platform system 10 consistent with the present disclosure is illustrated. It should be noted that the platform system 10 illustrated in the figures of the present disclosure is one of many different embodiments of platform systems that may be included in a system consistent with the present disclosure. Accordingly, a variety of different configurations and mounting orientations may be included with a system described herein.

Generally, the measurement system 10 may include a stage 12 for supporting a manufactured part (not shown) thereon. The stage 12 may be multi-axis having three orthogonal axes X, Y and Z of translation (i.e. linear motion). It should be noted that the stage 12 may include fewer axes of translation or one or more additional axes of rotation (i.e., angular motion). A variety of manual controls 13 may be associated with the stage 12 to adjust the position of the manufactured part. The manual controls 13 may include motors, actuators, or the like for automatically positioning and/or moving the manufactured part under inspection. In addition, at least the linear motion axes X and Y may be equipped with graduated linear encoders (not shown) for measuring the changes in the position of the manufactured part.

The measurement system 10 may further include at least on light source 14 configured to impart light upon and illuminate the manufactured part. The light source 14 may include, but is not limited to, light emitting diode (LED), incandescent and arc lamps. The measurement system 10 may further include an optical video system 16 configured to capture one or more images and/or video of the manufactured part. As shown, the optical video system 16 may be enclosed within a housing 18 of the measurement system 10. The captured images may be displayed on a monitor 20 upon which an operator may view the manufactured part.

The measurement system 10 may further include a data processing system (e.g., but not limited to, a computer) (not shown) including a database of digital representations (e.g. CAD drawings) of manufactured parts. The data processing system may be configured to receive one or more images of the manufactured part and transmit the one or more images to the monitor 20 to be displayed. The data processing system may further be configured to transmit a corresponding CAD drawing or measurement information to the monitor 20. The CAD drawing may be digitally overlaid on the image of the manufactured part and a comparison of the manufactured part against the corresponding CAD drawing may be made. In addition to providing a visual display of the captured images of the manufactured part and a corresponding CAD drawing, the monitor 20 may provide a means of operator input. For example, in one embodiment, the monitor 20 may provide a touchscreen interface upon which an operator may interact with and manipulate the content (i.e. video images of the manufactured part and CAD drawing) being displayed. The touchscreen interface may further allow an operator to interact with (e.g. command input) software for measurement and comparison of the manufactured part with the corresponding CAD drawing.

As generally understood, the data processing system may include custom, proprietary, known and/or after-developed surface and edge detection processing code (or instruction sets) that are generally well-defined and operable to measure the dimensions of the manufactured part and produce sub-pixel accurate measurements. The data processing system may further include custom, proprietary, known and/or after-developed processing code (or instruction sets) that are generally well-defined and operable to import and overlay a corresponding CAD drawing with respect to the manufactured part and to compare dimensions (e.g. measurements and geometry) of the manufactured part against the corresponding CAD drawing. Commercially available software may be used for the measurement and/or comparison of the manufactured part against a corresponding CAD drawing overlay. For example, a data processing system consistent with the present disclosure may include M3 series performance metrology software for video and optical measuring systems offered by MetLogix (Manchester, N.H., USA).

The data processing system may include a storage medium configured to store captured images and/or video of the manufactured part. More specifically, the data processing system may be configured to store captured images and/or video of the manufactured part with or without the CAD drawing overlay, as well as corresponding measurements and data.

Figure 2:
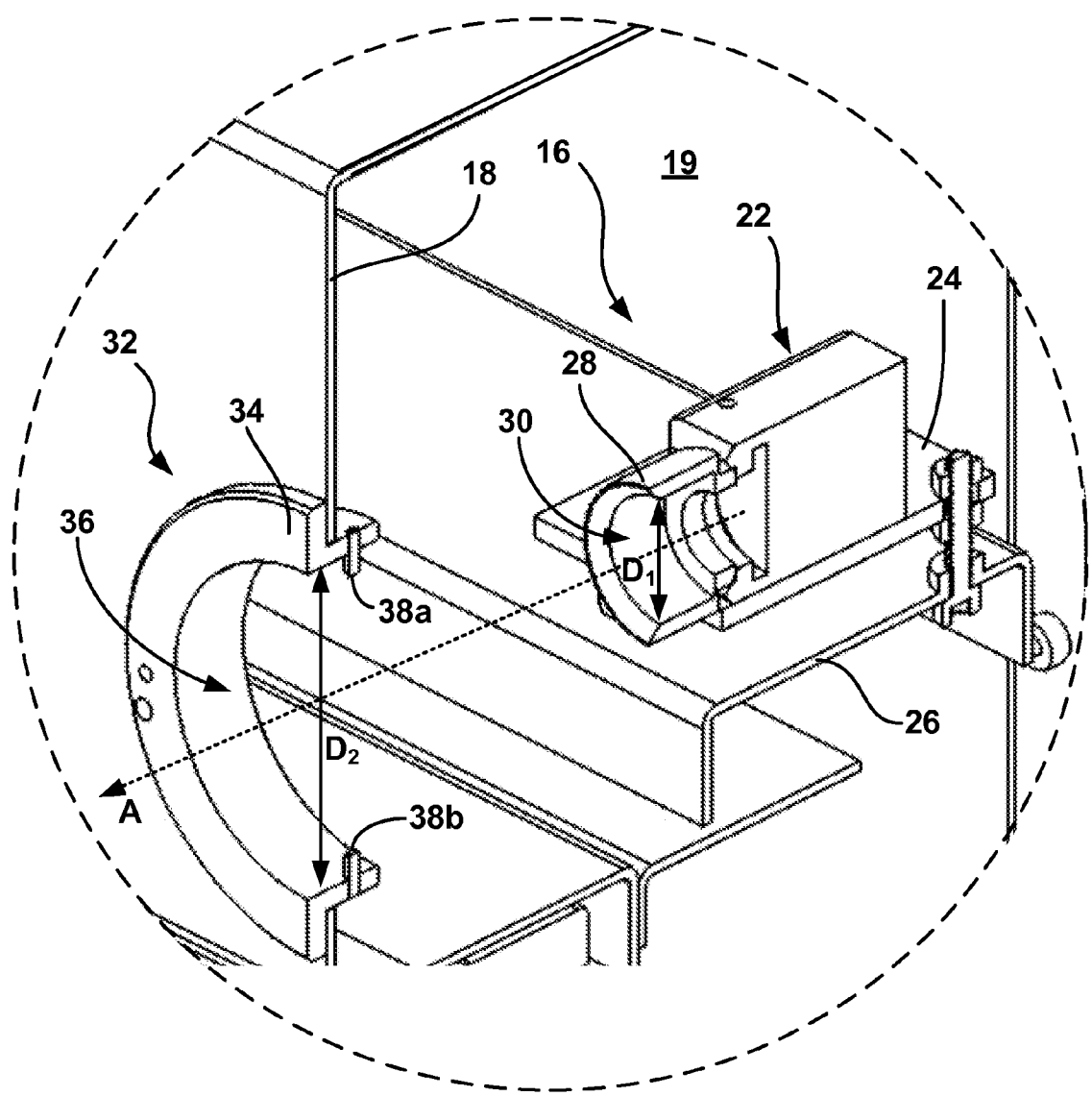
FIG. 2 is an enlarged perspective view, partly in section, of the optical system of the digital video measurement system of FIG. 1.

Turning to FIG. 2, an enlarged perspective view, partly in section, of the optical video system 16 consistent with the present disclosure is illustrated. In the illustrated embodiment, the optical video system 16 may include a digital camera 22 configured to capture digital images representative of the manufactured part. The camera 22 may include a video camera (e.g., camera configured to capture moving images comprised of a plurality of frames). More specifically, the digital camera 22 may be configured to capture hi-resolution images in real-time (i.e. at or near the camera's full frame rate) for a live video image of the manufactured part. Alternatively (or in addition) the digital camera 22 may include a still camera (e.g., camera configured to capture still photographs). The camera 22 may be configured to operate using light in the visible spectrum or with other portions of the electromagnetic spectrum not limited to the infrared spectrum, ultraviolet spectrum, etc.

As shown, the camera 22 may be disposed within an interior portion 19 of the housing 18 of the measurement system 10. The camera 22 may be fixed to an adjustable plate 24 coupled to a mounting bracket 26 within the housing 18. As described in greater detail herein, the elevation and/or levelness of the camera 22 may be adjusted by way of the adjustable plate 24 in relation to the manufactured part. The camera 22 may include a coupling member 28 extending from a portion thereof. The coupling member 28 may include a cavity 30 sized and/or shaped to receive a portion of a lens assembly (shown in FIG. 4). As shown, the cavity 30 may have a substantially cylindrical cross-section and may have a first diameter $D_1$. As described in greater detail herein, the coupling member 28 may represent a female side of a bayonet mount, wherein the coupling member 28 is configured to receive and retain a male side (e.g. first flange member 52) of the lens assembly (shown in FIG. 4).

In the illustrated embodiment, the measurement system 10 may further include a mounting assembly 32 disposed on a portion of the housing 18. The mounting assembly 32 may be disposed proximate the stage 12. As shown, the mounting assembly 32 may include a flange member 34 defining a longitudinally disposed passageway 36. The passageway 36 may extend from an exterior of the housing 18 to the interior 19 of the housing 18. As shown, the passageway 36 may be generally aligned with an optical axis A of the camera 22. The passageway 36 may have a substantially cylindrical cross-section and may have a second diameter $D_2$. The mounting assembly 32 may further include first and second protrusions 38a, 38b extending inwardly from the flange member 34 towards a center of the passageway 36. As described in greater detail herein, the mounting assembly 32 may be configured to receive and retain a portion of the lens assembly and maintain alignment of the lens assembly with the camera 22.

Figure 3:
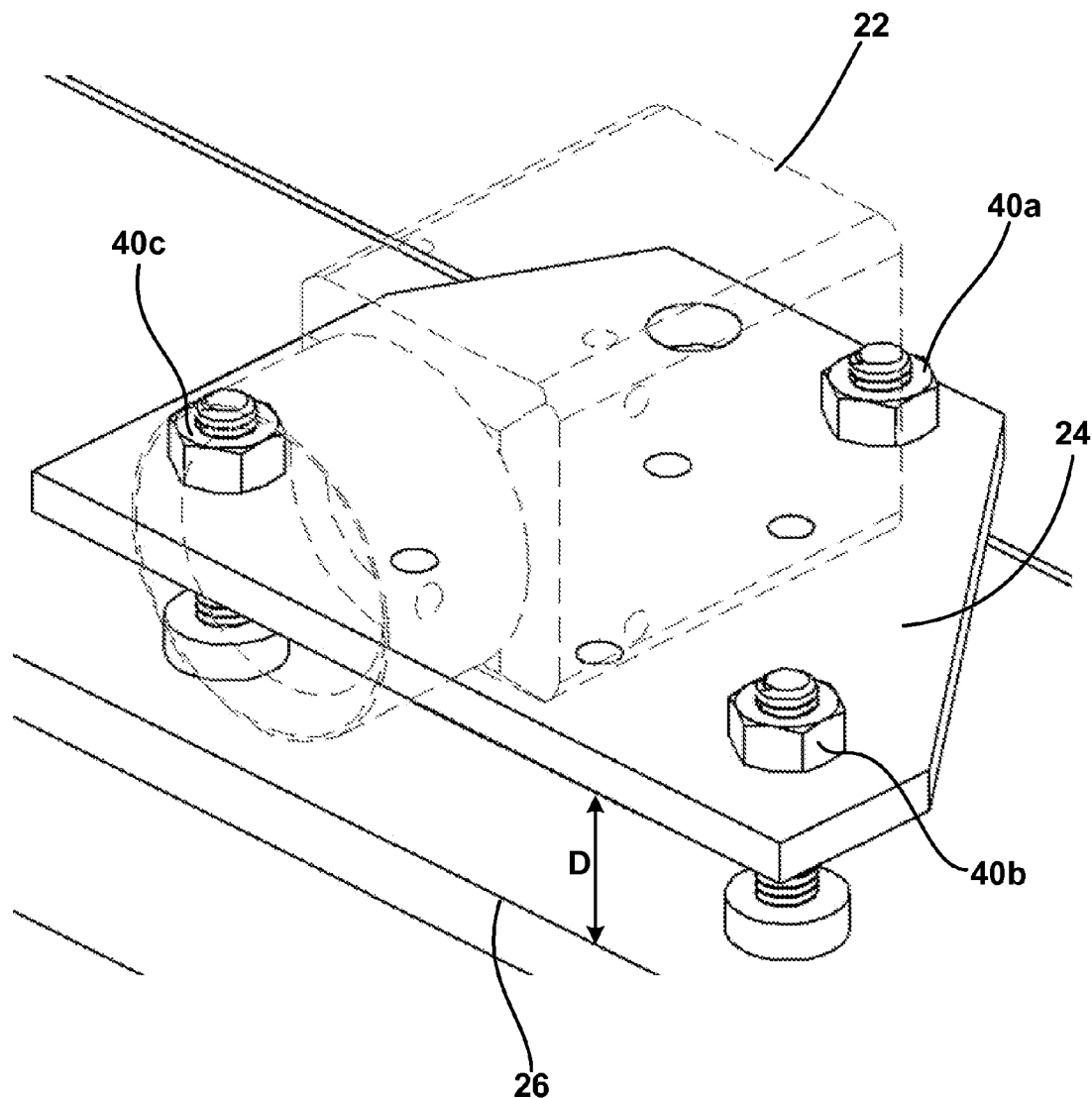
FIG. 3 is a perspective view of the digital camera of the optical video system.

Turning now to FIG. 3, a perspective view of the digital camera 22 coupled to the adjustable plate 24 is generally illustrated. As shown, the adjustable plate 24 is coupled to the mounting bracket 26 by way of one or more adjusting assemblies 40a-40c. As shown, the adjusting assemblies 40a-40c are nut and bolt assemblies. In the illustrated embodiment, the bolt portion may be fixed to the mounting bracket 26 and the nut portion may be adjusted (i.e. rotated about the threaded bolt) in order to adjust the distance D between the adjustable plate 24 and the mounting bracket 26. In turn, the elevation, as well as optical axis A, of the camera 22 may be adjusted in relation to the passageway 36 of the flange member 34, and ultimately in relation to the manufactured part. As generally understood by one skilled in the art, other known means of adjusting the plate 24 in relation to the mounting bracket 26 may be used. It should be noted that, although shown to be mounted in a horizontal orientation, the optical video system 16, including the camera 22 and lens assembly, may be configured to be mounted in a vertical orientation.

Figure 4:
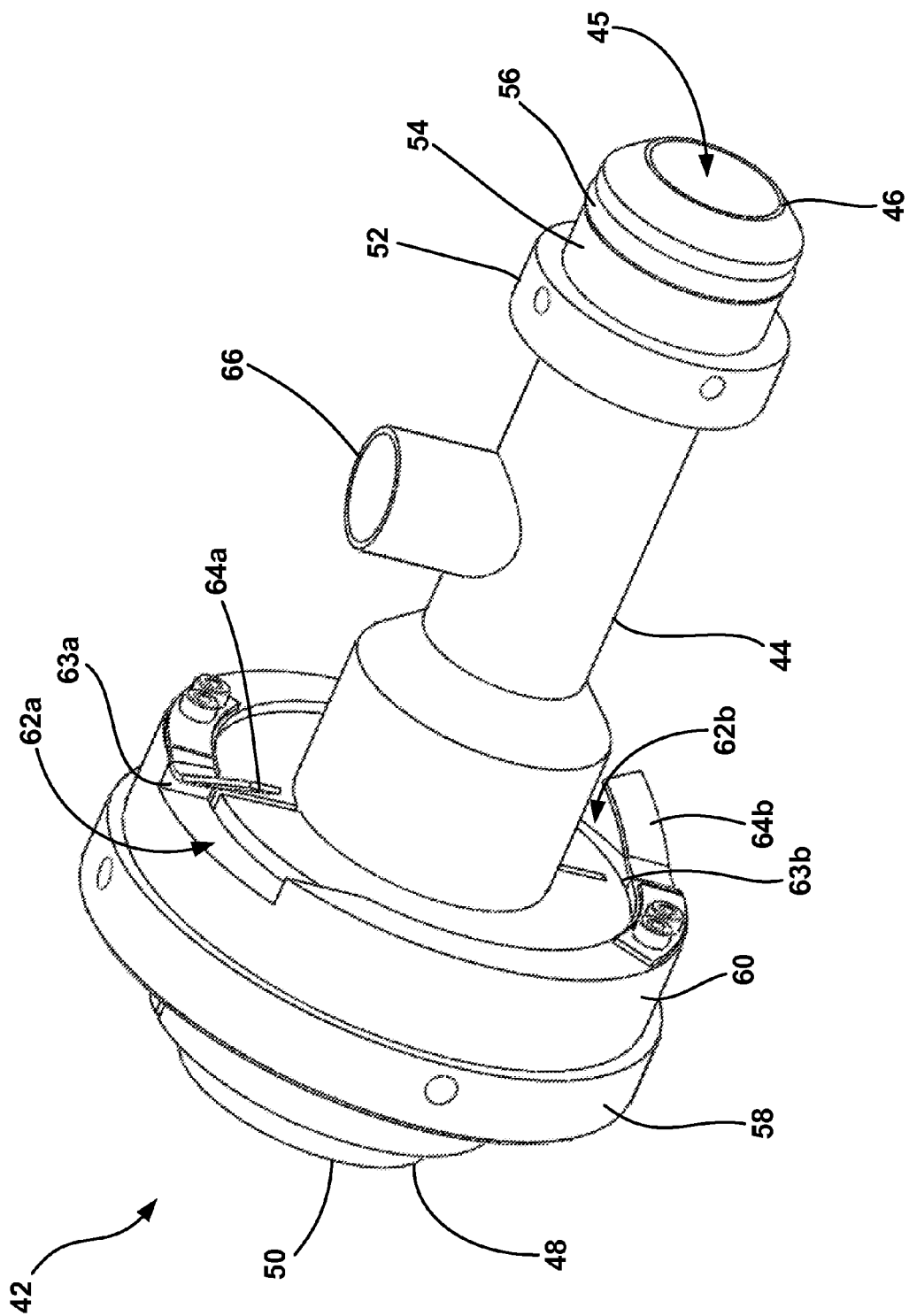
FIG. 4 is a perspective view of an interchangeable lens consistent with the present disclosure.

Turning now to FIG. 4, a perspective view of an interchangeable lens assembly 42 consistent with the present disclosure is illustrated. Generally, the lens assembly 42 may include a body 44 having a proximal end 46 and a distal end 48 and a substantially cylindrical passageway 45 longitudinally disposed within said body 44 and extending from the proximal end 46 to the distal end 48. As shown, an optic, such as a lens 50, may be positioned adjacent the distal end 48. As generally understood, the lens 50 may be configured to magnify the manufactured part and to provide a magnified image to be captured by the camera 22. In one embodiment, the lens 50 may include telecentric properties.

As shown, the lens assembly 42 may include a first flange member 52 disposed adjacent to the proximal end 46 of the body 44. As previously described, the first flange member 52 may represent a male side of a bayonet mount and be configured to be removably secured to the coupling member 28 (e.g. female side of the bayonet mount) of the camera 22. In particular, the first flange member 52 may include a coupling member 54 extending therefrom. The coupling member 54 may be shaped and/or sized to be received within the cavity 30 of the coupling member 28. The coupling member 54 may further include fastening member 56 configured to be disposed between a surface of the coupling member 54 and an interior surface of the cavity 30 when the coupling member 54 is received within the cavity 30. The fastening member 56 may be configured to secure and retain a portion (i.e. proximal end 46) of the lens assembly 42 to the camera 22 and to prevent undesired movement of the lens assembly 42 when coupled to the camera 22.

The fastening member 56 may include a resilient and durable material capable of elastic expansion when a force is applied thereto and elastic recovery when the force is removed therefrom. The material may include, but is not limited to, either natural or synthetic materials such as polymers and/or co-polymers. Examples may include polyurethane, latex, natural rubber, nylon (polyamides), polyester, polyethylene, polypropylene, PVC, fluoroplastics, block copolymers, polyethers and composites thereof. In the illustrated embodiment, the fastening member 56 may include an o-ring. It should be noted that other known means of releasably coupling the distal end 46 of the lens assembly 42 to the camera 22 may be included.

As shown, the lens assembly 42 may further include a second flange member 58 disposed adjacent to the distal end 48 of the body 44. The second flange member 58 may include a coupling member 60 extending therefrom. The coupling member 60 may be configured to be coupled to the flange member 34 of the mounting assembly 32. More specifically, the coupling member 60 may be shaped and/or sized to be received within the passageway 36 of the flange member 34. The coupling member 60 may further include first and second recesses 62a, 62b partially defined on a perimeter of the coupling member 60. The first and second recesses 62a, 62b may be configured to receive a portion of the first and second protrusions 38a, 38b extending from the flange member 34 of the mounting assembly 32. The first and second recesses 62a, 62b may further include first and second engagement portions 63a, 63b configured to engage the first and second protrusions 38a, 38b, respectively, when the coupling member 60 moves from a first position (e.g. non-engaged state) to a second position (e.g. engaged state) in relation to the flange member 34, as described in greater detail herein.

The coupling member 60 may further include first and second retaining members 64a, 64b positioned proximate to the first and second recesses 62a, 62b, respectively. As described in greater detail herein, the first and second retaining members 64a, 64b may be configured to engage and apply a force against the first and second protrusions 38a, 38b when the coupling member 60 moves from the first position to the second position and the first and second protrusions 38a, 38b contact the first and second engagement portions 63a, 63b. When the coupling member 60 is in the second position, the first and second retaining member 64a, 64b are configured to secure and retain a portion (i.e. distal end 48) of the lens assembly 42 to the mounting assembly 32 and to prevent undesired movement of the lens assembly 42. Further, alignment of the lens assembly 42 with the camera 22 may be maintained by the coupling of the lens assembly 42 to the mounting assembly 32.

As shown, the body 44 may further include a co-axial attachment member 66 configured to receive and retain co-axial attachments (not shown) thereto. As generally understood, co-axial attachments may include, but are not limited to, any known co-axial illumination attachments, for example.

As described in greater detail herein, a variety of different interchangeable lens assemblies (shown in FIG. 7) may be releasably coupled to the camera 22 by way of the bayonet-style mounting means. In particular, each of the interchangeable lens assemblies may include first flange member (representing the male side) similar to the first flange member 52 as shown and described with respect to FIG. 4, wherein the first flange member is configured to be releasably coupled to the coupling member 28 (representing the female side) of the camera 22. Use of the bayonet-style mounting means allows the variety of different lens assemblies to be interchangeably coupled to the camera 22 in a consistently precise and relatively simple manner. Additionally, each of the interchangeable lens assemblies may further include a second flange member similar to the second flange member 58 as shown and described with respect to FIG. 4, wherein the second flange member may be configured to be releasably coupled to the flange member 34 of the mounting assembly 32.

Figure 5:
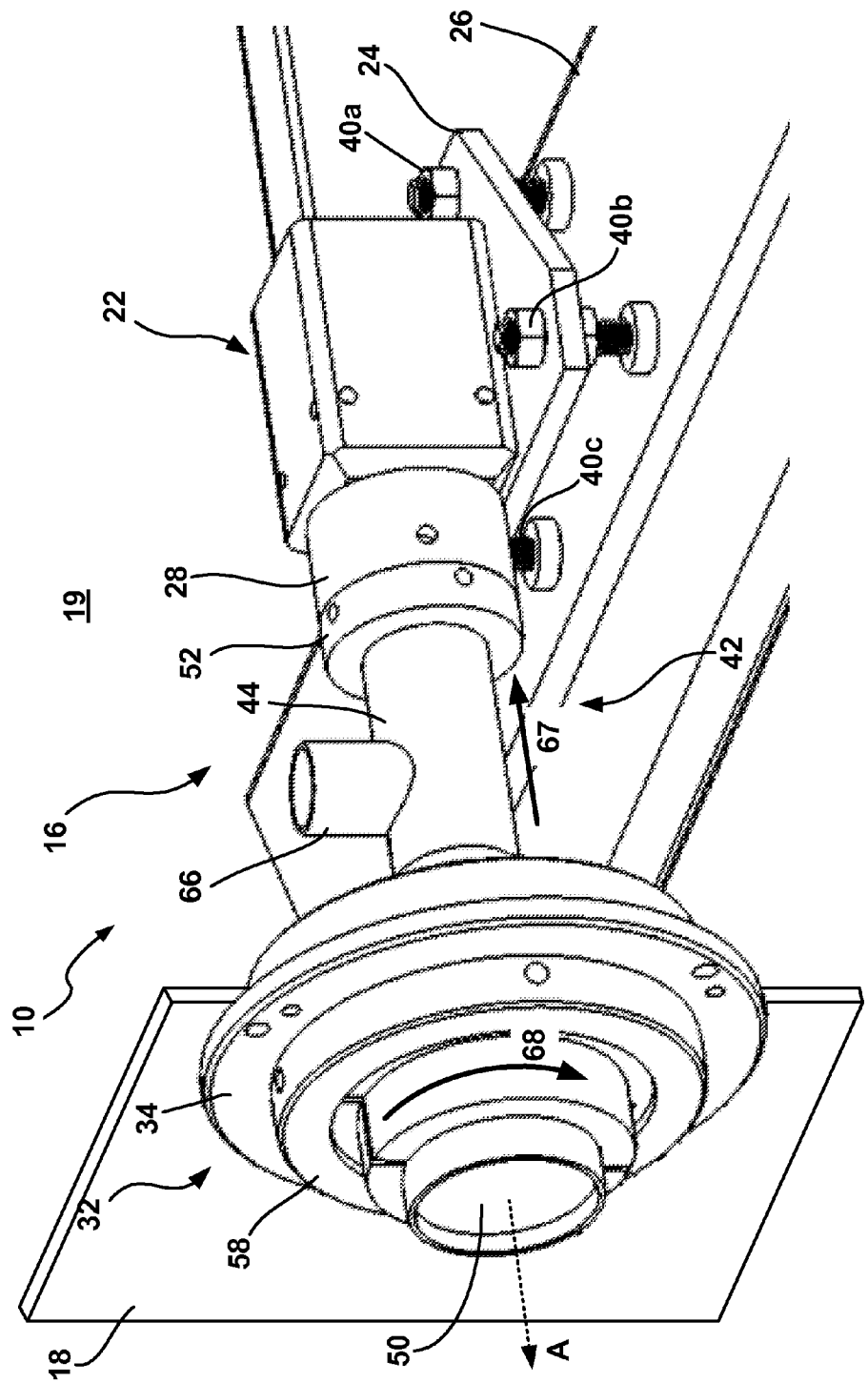
FIG. 5 is a perspective view of the optical video system in an assembled state illustrating the interchangeable lens assembly coupled to the mounting assembly and digital camera consistent with the present disclosure.
Figure 6:
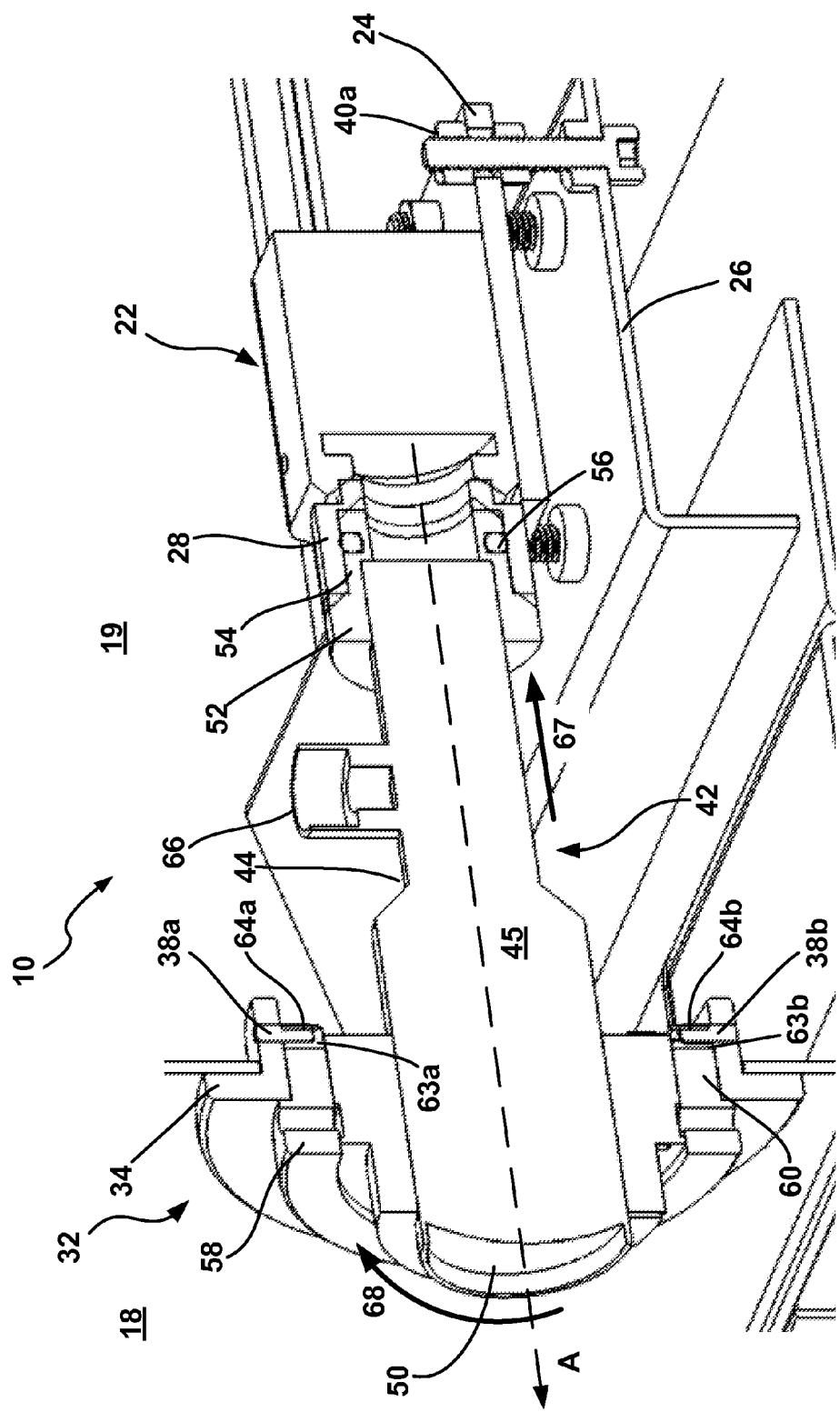
FIG. 6 is a perspective view, partly in section, of the optical video system of FIG. 5.

FIG. 5 is a perspective view of the optical video system 16 in an assembled state and FIG. 6 is a perspective view, partly in section, of the assembled optical video system 16. As shown, the lens assembly 42 is coupled to the mounting assembly 32 and the camera 22 such that the passageway 45 of the body 44 of the lens assembly 42 is generally aligned with the optical axis A of the camera 22.

As previously described, the camera 22 and mounting assembly 32 may be configured to allow a variety of interchangeable lenses (shown in FIG. 7) to be relatively quickly and easily coupled to and decoupled from the mounting assembly 32 and digital camera 22 as needed. In the illustrated embodiment, the lens assembly 42 may be coupled to at least the camera 22 by moving the lens assembly 42 in a direction towards the camera 22, as indicated by arrow 67, such that the coupling member 54 of the first flange member 52 of the lens assembly 42 is received within the cavity 30 of the coupling member 28 of the camera 22. The fastening member 56 may elastically deform as the coupling member 54 is received within the cavity 30 and may secure and retain the coupling member 54, and proximal end 46, of the lens assembly 42 to the camera 22. As shown, the first flange member 52 of the lens assembly 42 and the flange member 28 of the camera 22 may engage one another and serve as an indication to the operator that the distal end 46 is securely coupled to the camera 22.

Additionally, as the lens assembly 42 moves into engagement with the camera 22, the lens assembly 42 may move into engagement with the mounting assembly 32. More specifically, as the lens assembly 42 moves in a direction towards the camera 22, as indicated by arrow 67, the first and second protrusions 38a, 38b of the flange member 34 may be received within the first and second recesses 62a, 62b of the coupling member 60, thereby placing the coupling member 60 of the lens assembly 42 in the first position. When in the first position, the lens assembly 42 is not securely coupled to the mounting assembly 32.

The coupling member 60 of the lens assembly 42 may be placed in a second position, in which the lens assembly 42 is securely coupled to the mounting assembly 32. More specifically, an operator may rotate the coupling member 60 about the optical axis A, as indicated by arrow 68, to move the coupling member 60 from the first position to the second position. As the coupling member 60 rotates, the first and second protrusions 38a, 38b are guided along the surface of the first and second recesses 62a, 62b until the protrusions 38a, 38b make contact with the engagement portions 63a, 63b. Additionally, as the coupling member 60 rotates from the first to the second position, the first and second retaining members 64a, 64b may be forced inwardly towards the first and second recesses 62a, 62b. When the first and second protrusions 38a, 38b contact the engagement portions 63a, 63b, the first and second retaining members 64a, 64b may be configured to engage and apply a force against the first and second protrusions 38a, 38b, thereby retaining the protrusions 38a, 38b within the associated recesses 62a, 62b and securely coupling the coupling member 60 and second flange member 58 to the flange member 34 of the mounting assembly 32.

The lens assembly 42 may be disengaged from the mounting assembly 32 by moving (e.g. rotating) the coupling member 60 from the second position to the first position. Similarly, the lens assembly 42 may be disengaged from the camera 22 by moving the lens assembly 42 in a direction away from the camera 22, thereby disengaging the coupling member 54 from the cavity 30 of the flange member 28.

Figure 7:
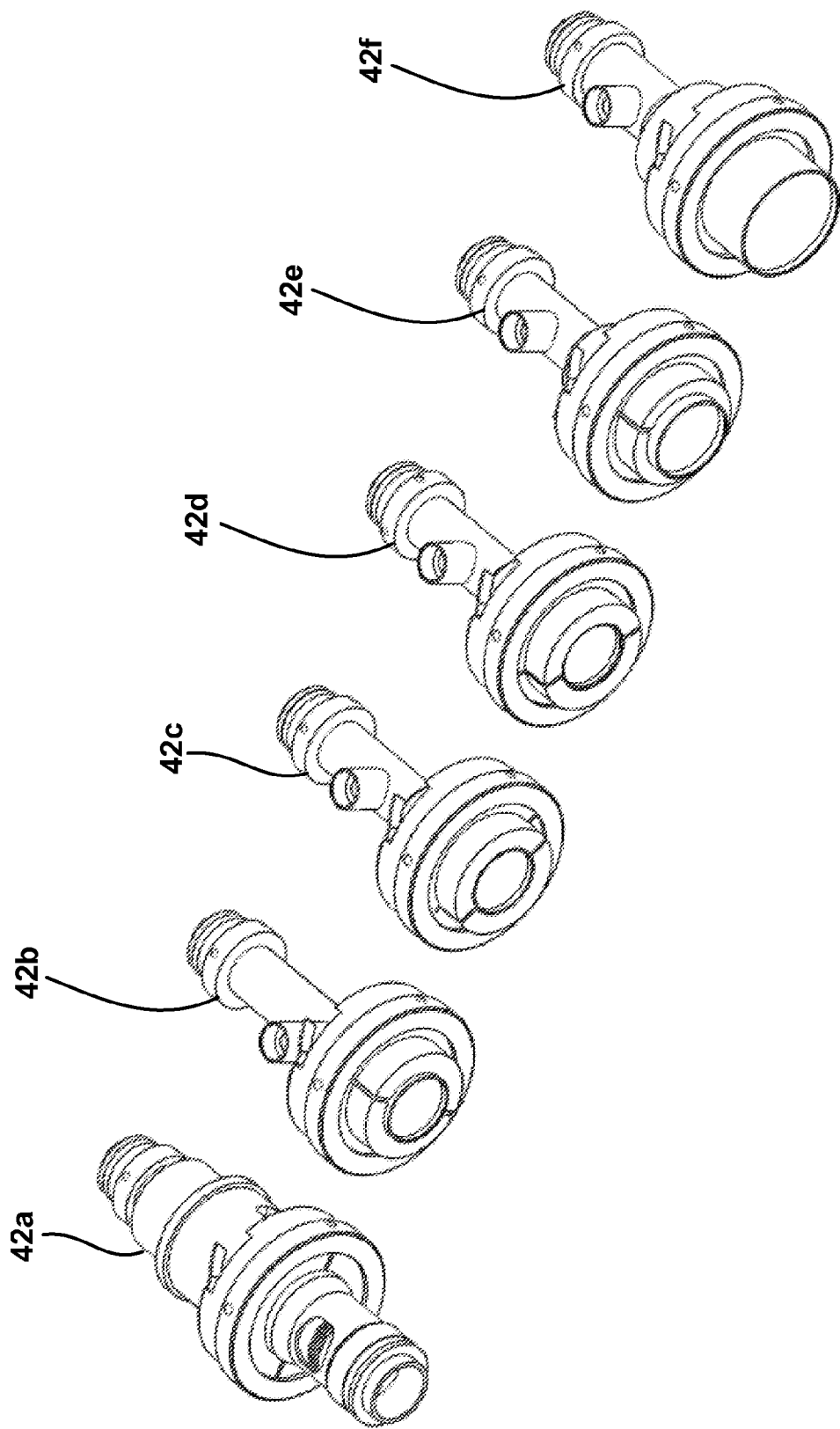
FIG. 7 is a perspective view of interchangeable lenses configured to be coupled to the digital camera and mounting assembly consistent with the present disclosure.

FIG. 7 is a perspective view of interchangeable lenses 42a-42f configured to be coupled to the digital camera 22 and mounting assembly 32 consistent with the present disclosure. As shown, each of the lenses 42a-42f may be readily interchangeable with the flange member 28 of the camera 22 and the flange member 34 of the mounting assembly 32 in a manner previously described herein. As generally understood, each of the lenses 42a-42f may have different optical properties from one another. For example, lenses 42b-42f may each have different optical magnification powers and/or ranges of optical magnification. Furthermore, one or more of the lenses, such as lens 42a, may have zooming capability.

According to one aspect of the disclosure, there is provided an optical video system. The optical video system includes a camera configured to capture one or more images of at least one object, the camera having a female coupling member extending from portion thereof, the coupling member including a cavity defined therein. The optical video system further includes at least one of a plurality of interchangeable lens assemblies configured to be coupled to the camera. Each interchangeable lens assembly includes a body having a proximal end and a distal end, a passageway longitudinally disposed and extending from the proximal end to the distal end of the body, a lens positioned adjacent to the distal end and configured to magnify the one or more objects and provide a magnified image to be captured by the camera and a first flange member disposed adjacent to the proximal end of the body and having a male coupling member extending therefrom in a direction away from the distal end of the body, the male coupling member is shaped and/or sized to be received within the cavity of the female coupling member of the camera and releasably couple the interchangeable lens assembly to the camera.

According to another aspect of the disclosure, there is provided a video measurement platform system. The video measurement platform system includes an optical video system for capturing one or more images representative of a manufactured part. The optical video system includes a camera configured to capture one or more images of the manufactured part, the camera having a female coupling member extending from portion thereof, the coupling member including a cavity defined therein. The optical video system further includes at least one of a plurality of interchangeable lens assemblies configured to be coupled to the camera. Each interchangeable lens assembly includes a body having a proximal end and a distal end, a passageway longitudinally disposed and extending from the proximal end to the distal end of the body, a lens positioned adjacent to the distal end and configured to magnify the manufactured part and provide a magnified image to be captured by the camera and a first flange member disposed adjacent to the proximal end of the body and having a male coupling member extending therefrom in a direction away from the distal end of the body, the male coupling member is shaped and/or sized to be received within the cavity of the female coupling member of the camera and releasably couple the interchangeable lens assembly to the camera. The video measurement platform system further includes a housing enclosing at least a portion of the camera within and a display for presenting at least the captured images of the manufactured part.

According to yet another aspect of the disclosure, there is provided a video measurement platform system. The video measurement platform system includes one or more light sources of imparting light upon and illuminating a manufactured part and a stage for supporting the manufactured part, the stage is configured to translate along at one linear motion axis. The video measurement platform system further includes an optical video system for capturing one or more images representative of a manufactured part. The optical video system includes a camera configured to capture one or more images of the manufactured part, the camera having a female coupling member extending from portion thereof, the coupling member including a cavity defined therein. The optical video system further includes at least one of a plurality of interchangeable lens assemblies configured to be coupled to the camera. Each interchangeable lens assembly includes a body having a proximal end and a distal end, a passageway longitudinally disposed and extending from the proximal end to the distal end of the body, a lens positioned adjacent to the distal end and configured to magnify the manufactured part and provide a magnified image to be captured by the camera and a first flange member disposed adjacent to the proximal end of the body and having a male coupling member extending therefrom in a direction away from the distal end of the body, the male coupling member is shaped and/or sized to be received within the cavity of the female coupling member of the camera and releasably couple the interchangeable lens assembly to the camera. The video measurement platform system further includes a display for presenting at least the captured images of the manufactured part.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

What is claimed is:

1. An optical video system comprising:
   a camera configured to capture one or more images of at least one object, said camera having a female coupling member extending from portion thereof, said female coupling member including a cavity defined therein; and
   at least one interchangeable lens assembly configured to be coupled to said camera, said at least one interchangeable lens assembly comprises:
      a body having a proximal end and a distal end;
      a passageway longitudinally disposed and extending from said proximal end to said distal end of said body;
      a lens positioned adjacent to said distal end and configured to magnify said one or more objects and provide a magnified image to be captured by said camera;
      a first flange member disposed adjacent to said proximal end of said body and having a male coupling member extending therefrom in a direction away from said distal end of said body, said male coupling member being shaped and/or sized to be received within said cavity of said female coupling member of said camera and releasably couple said at least one interchangeable lens assembly to said camera; and
      a second flange member disposed adjacent to said distal end of said body and having a coupling member extending therefrom, said coupling member being configured to be coupled to a mounting assembly.

2. The optical video system of claim 1, wherein said at least one interchangeable lens assembly further comprises a fastening member positioned on a portion of said male coupling member, said fastening member being configured to be disposed between a surface of the male coupling member and an interior surface of said cavity of said female coupling member when said male coupling member is received within said female coupling member.

3. The optical video system of claim 2, wherein said fastening member is configured to secure and retain at least said proximal end of said at least one interchangeable lens assembly to said camera to prevent undesired movement of said at least one interchangeable lens assembly when coupled to said camera.

4. The optical video system of claim 2, wherein said fastening member comprises a resilient and durable material capable of elastic expansion when a force is applied thereto and elastic recovery when the force is removed therefrom.

5. The optical video system of claim 4, wherein said material is selected from the group consisting of polyurethane, latex, natural rubber, nylon, polyester, polyethylene, polypropylene, PVC, fluoroplastics, block copolymers, polyethers and composites thereof.

6. The optical video system of claim 1, wherein said mounting assembly is disposed on a portion of a housing enclosing said camera within, said mounting assembly having a flange member defining a longitudinally disposed passageway aligned with an optical axis of said camera, said passageway being shaped and/or sized to receive and retain at least said coupling member of said second flange and maintain alignment of said at least one interchangeable lens assembly with said camera.

7. The optical video system of claim 1, wherein said coupling member of said second flange member comprises:
   first and second recesses defined along a perimeter of said coupling member;
   first and second engagement portions defined on a portion of said first and second recesses, respectively; and
   first and second retaining members positioned proximate to said first and second recesses, respectively.

8. The optical video system of claim 7, wherein at least said coupling member of said second flange member is configured to move between a first position, in which said coupling member is in a non-engaged state with said flange member of said mounting assembly, and a second position, in which said coupling member is in an engaged state with said flange member of said mounting assembly.

9. The optical video system of claim 8, wherein said first and second recesses are configured to receive first and second protrusions extending inwardly from said flange member of said mounting assembly towards a center of said passageway, and wherein, when said coupling member moves from said first position to said second position, said first and second engagement portions are configured to engage said first and second protrusions and said first and second retaining members of said coupling member are configured to engage and apply a force against said first and second protrusions and secure and retain said distal end of said at least one interchangeable lens assembly to said mounting assembly to prevent undesired movement of said at least one interchangeable lens assembly and maintain alignment of said at least one interchangeable lens assembly with said camera.

10. The optical video system of claim 9, wherein said passageway of said body of said at least one interchangeable lens assembly is configured to align with an optical axis of said camera.

11. A video measurement platform system comprising:
   an optical video system for capturing one or more images representative of a manufactured part, said optical video system comprising:

a camera configured to capture one or more images of said manufactured part, said camera having a female coupling member extending from portion thereof, said female coupling member including a cavity defined therein; and at least one interchangeable lens assembly configured to be coupled to said camera, said at least one interchangeable lens assembly comprises:

a body having a proximal end and a distal end;

a passageway longitudinally disposed and extending from said proximal end to said distal end of said body;

a lens positioned adjacent to said distal end and configured to magnify said manufactured part and provide a magnified image to be captured by said camera;

a first flange member disposed adjacent to said proximal end of said body and having a male coupling member extending therefrom in a direction away from said distal end of said body, said male coupling member being shaped and/or sized to be received within said cavity of said female coupling member of said camera and releasably couple said at least one interchangeable lens assembly to said camera; and a second flange member disposed adjacent to said distal end of said body and having a coupling member extending therefrom, said coupling member being configured to be coupled to a mounting assembly;

a housing enclosing at least a portion of said camera within; and a display for presenting at least said captured images of said manufactured part.

12. The video measurement platform system of claim 11, wherein said at least one interchangeable lens assembly further comprises a fastening member positioned on a portion of said male coupling member, said fastening member being configured to be disposed between a surface of the male coupling member and an interior surface of said cavity of said female coupling member when said male coupling member is received within said female coupling member.

13. The video measurement platform system of claim 12, wherein said fastening member is configured to secure and retain at least said proximal end of said at least one interchangeable lens assembly to said camera prevent undesired movement of said at least one interchangeable lens assembly when coupled to said camera.

14. The video measurement platform system of claim 11, wherein the mounting assembly is disposed on a portion of said housing, and wherein said flange member defines a longitudinally disposed passageway aligned with an optical axis of said camera, said passageway being shaped and/or sized to receive and retain a portion of said at least one interchangeable lens assembly and maintain alignment of said at least one interchangeable lens assembly with said camera.

15. The video measurement platform system of claim 14, wherein said coupling member is configured to be received within said longitudinally disposed passageway and releasably coupled to said flange member of said mounting assembly, wherein at least said coupling member is configured to move between a first position, in which said coupling member is in a non-engaged state with said flange member of said mounting assembly, and a second position, in which said coupling member is in an engaged state with said flange member of said mounting assembly.

16. The video measurement platform system of claim 11, wherein said coupling member of said second flange member comprises:

first and second recesses defined along a perimeter of said coupling member;

first and second engagement portions defined on a portion of said first and second recesses, respectively; and first and second retaining members positioned proximate to said first and second recesses, respectively.

17. The video measurement platform system of claim 16, wherein said first and second recesses are configured to receive first and second protrusions extending inwardly from said flange member of said mounting assembly towards a center of said passageway, and wherein, when said coupling member moves from said first position to said second position, said first and second engagement portions are configured to engage said first and second protrusions and said first and second retaining members of said coupling member are configured to engage and apply a force against said first and second protrusions and secure and retain said distal end of said at least one interchangeable lens assembly to said mounting assembly to prevent undesired movement of said at least one interchangeable lens assembly and maintain alignment of said at least one interchangeable lens assembly with said camera.

18. A video measurement platform system comprising:

one or more light sources of imparting light upon and illuminating a manufactured part;

a stage for supporting said manufactured part, said stage being configured to translate along at one linear motion axis;

an optical video system for capturing one or more images representative of said manufactured part, said optical video system comprising:

a camera configured to capture one or more images of said manufactured part, said camera having a female coupling member extending from portion thereof, said female coupling member including a cavity defined therein; and at least one interchangeable lens assembly configured to be coupled to said camera, said at least one interchangeable lens assembly comprises:

a body having a proximal end and a distal end;

a passageway longitudinally disposed and extending from said proximal end to said distal end of said body;

a lens positioned adjacent to said distal end and configured to magnify said manufactured part and provide a magnified image to be captured by said camera;

a first flange member disposed adjacent to said proximal end of said body and having a male coupling member extending therefrom in a direction away from said distal end of said body, said male coupling member being shaped and/or sized to be received within said cavity of said female coupling member of said camera and releasably couple said at least one interchangeable lens assembly to said camera; and a second flange member disposed adjacent to said distal end of said body and having a coupling member extending therefrom, said coupling member being configured to be coupled to a mounting assembly; and a display for presenting at least said captured images of said manufactured part.

19. The video measurement platform system of claim 18, further comprising an adjustable plate configured to be coupled to a portion of said camera and provide support and movement of said camera in relation to said manufactured part.

20. The video measurement platform system of claim 18, wherein the said at least one interchangeable lens assembly comprises two or more interchangeable lens assemblies.

* * * * *